(12) United States Patent
Copp-Howland

(10) Patent No.: US 8,017,042 B2
(45) Date of Patent: Sep. 13, 2011

(54) MEDICAL ELECTRODE CONTAINING A HYDROPHILIC POLYMER

(75) Inventor: Warren W. Copp-Howland, Chicopee, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/797,694

(22) Filed: Jun. 10, 2010

(65) Prior Publication Data

US 2010/0308282 A1    Dec. 9, 2010

Related U.S. Application Data

(63) Continuation of application No. 11/442,797, filed on May 30, 2006, now Pat. No. 7,761,131.

(51) Int. Cl.
*H01B 1/00* (2006.01)
*A61B 5/04* (2006.01)

(52) U.S. Cl. .................. 252/500; 600/391; 600/397

(58) Field of Classification Search ....... 252/500–521.6; 600/391, 397

See application file for complete search history.

(56) References Cited

U.S. PATENT DOCUMENTS

| | | | |
|---|---|---|---|
| 4,768,523 A | 9/1988 | Cahalan et al. | |
| 4,911,855 A | 3/1990 | Rasicci et al. | |
| 5,173,302 A | 12/1992 | Holmblad et al. | |
| 5,234,992 A | 8/1993 | Gyory et al. | |
| 5,338,490 A | 8/1994 | Dietz et al. | |
| 5,674,275 A | 10/1997 | Tang et al. | |
| 5,721,313 A | 2/1998 | Yeung et al. | |
| 5,779,632 A | 7/1998 | Dietz et al. | |
| 5,985,990 A | 11/1999 | Kantner et al. | |
| 6,038,464 A | 3/2000 | Axelgaard et al. | |
| 6,263,226 B1 | 7/2001 | Axelgaard et al. | |
| 6,447,798 B1 | 9/2002 | Munro et al. | |
| 6,592,898 B2 | 7/2003 | Munro et al. | |

(Continued)

FOREIGN PATENT DOCUMENTS

WO    WO 88/05666 A1    8/1988

(Continued)

OTHER PUBLICATIONS

Search Report from corresponding European Application No. EP 10 16 0096 mailed Apr. 4, 2011.

(Continued)

*Primary Examiner* — Mark Kopec
*Assistant Examiner* — Jaison Thomas
(74) *Attorney, Agent, or Firm* — Lisa E. Winsor, Esq.

(57) ABSTRACT

Conductive compositions whose electrical properties do not change significantly due when stored open to the atmosphere, methods for preparing the compositions, and medical electrodes that comprise the compositions are disclosed. The compositions are hydrogels that comprise about 33 wt % to about 68 wt % of a humectant or a mixture of humectants; about 1 wt % to about 8 wt % of an electrolyte or mixture of electrolytes; about 6 wt % to about 20 wt % of water; about 18 wt % to about 45 wt % of a copolymer. The copolymer comprises, in polymerized form, about 80 mol % to about 95 mol % of a first monomer, which is a mixture of acrylic acid and a salt thereof, about 5 mol % to 20 mol % of a second monomer, preferably a salt of 2-acrylamido-2-methylpropane sulfonic acid, and, optionally a crosslinking agent. The conductive composition has a pH of about 7.0 or less.

9 Claims, 1 Drawing Sheet

U.S. PATENT DOCUMENTS

| | | |
|---|---|---|
| 6,613,030 B1 | 9/2003 | Coles et al. |
| 6,641,569 B1 | 11/2003 | Coles et al. |
| 6,683,120 B2 | 1/2004 | Munro et al. |
| 6,792,301 B2 | 9/2004 | Munro et al. |
| 6,887,917 B2 | 5/2005 | Yang et al. |
| 6,987,133 B2 | 1/2006 | Chen |
| 7,076,282 B2 | 7/2006 | Munro et al. |
| 7,620,439 B2 | 11/2009 | Menon et al. |
| 2002/0034492 A1* | 3/2002 | Munro et al. ............ 424/78.36 |
| 2003/0232895 A1 | 12/2003 | Omidian et al. |
| 2005/0085706 A1 | 4/2005 | Perrault et al. |
| 2005/0136023 A1* | 6/2005 | Yahiaoui et al. ........... 424/70.13 |
| 2005/0136077 A1 | 6/2005 | Yahiaoui et al. |
| 2005/0249790 A1* | 11/2005 | Weidl et al. ................ 424/443 |
| 2005/0277991 A1 | 12/2005 | Covey et al. |
| 2006/0258788 A1* | 11/2006 | Coggins et al. ............. 524/386 |
| 2007/0196320 A1* | 8/2007 | Yasin ............................. 424/77 |
| 2007/0208130 A1 | 9/2007 | Sasahara et al. |
| 2007/0282188 A1 | 12/2007 | Copp-Howland |
| 2007/0282408 A1 | 12/2007 | Coggins |

FOREIGN PATENT DOCUMENTS

| | | |
|---|---|---|
| WO | WO 93/09713 | 5/1993 |
| WO | WO 2007/063436 A1 | 6/2007 |
| WO | WO 2007/083275 A1 | 7/2007 |
| WO | WO 2007/142797 A2 | 12/2007 |

OTHER PUBLICATIONS

Monroe, B.M., et al. "Photoinitiators for Free-Radical Initiated Photoimaging Systems," *Chem.Rev.*, vol. 93, pp. 435-448 (1993).

Office Action issued in U.S. Appl. No. 12/208,424 mailed Mar. 5, 2009 (8 pages).

Office Action issued in U.S. Appl. No. 12/208,424 mailed Sep. 17, 2009 (8 pages).

Final Office Action issued in U.S. Appl. No. 12/208,424 mailed Apr. 13, 2010 (13 pages).

Claims from co-pending U.S. Appl. No. 12/208,424 (8 pages), Jun. 11, 2010.

* cited by examiner

MEDICAL ELECTRODE CONTAINING A HYDROPHILIC POLYMER

RELATED APPLICATION

This application is a continuation application under 35 U.S.C. 120 and claims the benefit to U.S. patent application Ser. No. 11/442,797 filed May 30, 2006 now U.S. Pat. No. 7,761,131, entitled MEDICAL ELECTRODE CONTAINING A HYDROPHILIC POLYMER, which is incorporated herein by reference in its entirety for all purposes.

FIELD OF THE INVENTION

This invention relates to medical electrodes. In particular, this invention relates to conductive compositions whose electrical properties do not change significantly when the composition is stored open to the atmosphere, to methods for making the compositions, and to medical electrodes that comprise the compositions.

BACKGROUND OF THE INVENTION

Medical electrodes are used to transmit electrical signals or currents between the body of a patient and external medical equipment. These electrodes typically comprise a conductive composition adhered to or otherwise in contact with, the skin of the patient, and a conductor, which is electrically connected to the conductive composition and to the external medical equipment.

The conductive compositions are typically water containing hydrogels. Water containing conductive compositions are subject to loss of water during storage. Because the electrical properties of the composition and, consequently, of the electrode are sensitive to the water content of the conducting composition, medical electrodes that contain such conductive compositions require expensive packaging, such as foil barrier packaging, to prevent water loss and, thus, attain reasonable shelf life. Thus, a need exists for a conductive composition that can be used in medical electrodes whose electrical properties do not change significantly when stored open to the atmosphere and, thus, can be packaged in less expensive packaging.

SUMMARY OF THE INVENTION

In one aspect, the invention is a conductive composition. The conductive composition comprises:
   about 33 wt % to about 68 wt % of a humectant or a mixture of humectants;
   about 1 wt % to about 8 wt % of an electrolyte or mixture of electrolytes;
   about 6 wt % to about 20 wt % of water;
   about 18 wt % to about 45 wt % of a copolymer comprising, in polymerized form, about 80 mol % to about 95 mol % of a first monomer, in which the first monomer is a mixture of acrylic acid and a salt thereof, and about 5 mol % to 20 mol % of a second monomer, in which the second monomer is one of more monomers selected from $CH_2=CHC(O)XR$, in which X is O or NH and R is an unsubstituted or substituted alkyl group of 1 to 5 carbon atoms; and
   in which the conductive composition has a pH of about 7.0 or less.

In another aspect the second monomer is a salt of 2-acrylamido-2-methylpropane sulfonic acid. In yet another aspect, the copolymer is a cross-linked copolymer that is cross-linked by a cross-linking agent. In still another aspect, the copolymer is not crosslinked by cross-linking agent.

In another aspect, the invention is a method for forming a conductive composition. The method comprises the steps of:
   a) preparing a pre-gel reaction mixture comprising:
      about 33 wt % to 68 wt % of a humectant;
      about 1 wt % to about 8 wt % of an electrolyte;
      about 2 wt % to 8 wt % sodium hydroxide;
      about 18 wt % to about 45 wt % of a monomer mix, the monomer mix comprising about 80 mol % to about 95 mol % of a first monomer, in which the first monomer is a mixture of acrylic acid and a salt thereof, and about 5 mol % to 20 mol % of a second monomer, in which the second monomer is one of more monomers selected from $CH_2=CHC(O)XR$, in which X is O or NH and R is an unsubstituted or substituted alkyl group of 1 to 5 carbon atoms;
      a polymerization initiator; and
      about 5 wt % to about 18 wt % water, exclusive of water formed by the neutralization of the part of the acrylic acid by the sodium hydroxide;
   b) polymerizing the monomer mix and crosslinking agent to form a copolymer in which the conductive composition has a pH of about 7.0 or less.

In another aspect, the monomer mix additionally comprises about 0.01 wt % to about 1 wt % of a crosslinking agent. In still another aspect, the monomer mix does not comprise a cross-linking agent.

In one aspect, the electrical properties of the conductive composition do not change significantly when the composition is stored open to the atmosphere. In another aspect, the invention is a medical electrode comprising the conductive composition. Thus, in other aspects, the invention is a composition and a biomedical electrode comprising the composition that meet ANSI/AAMI standard EC 12:2000, both before and after storage open to the atmosphere at 70° C. for 72 hr.

DETAILED DESCRIPTION OF THE INVENTION

Figure 1:
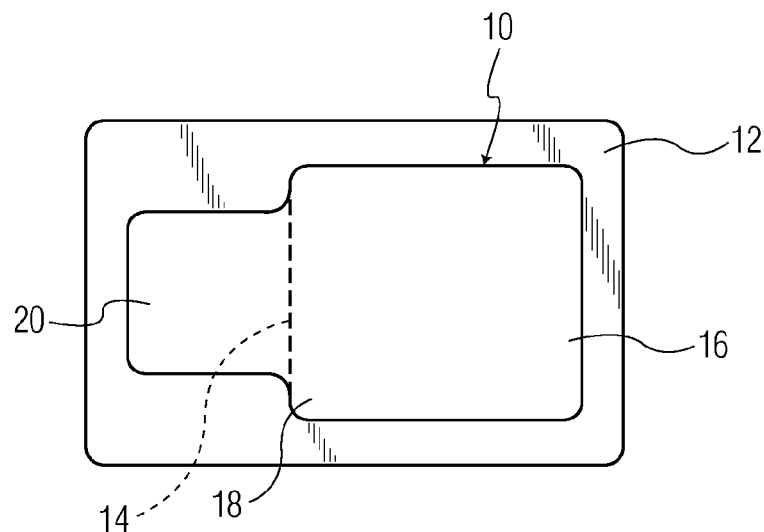
FIG. 1 is a top plan view of a medical electrode comprising the conductive composition.

Unless the context indicates otherwise, in the specification and claims, the terms first monomer, second monomer, humectant, electrolyte, polymerization initiator, polymerization inhibitor, crosslinking agent, neutralizer, salt, and similar terms also include mixtures of such materials. Unless otherwise specified, all percentages are percentages by weight and all temperatures are in degrees Centigrade (degrees Celsius).

Conductive Composition

The conductive composition, sometimes known as a hydrogel or a conductive hydrogel, is prepared by polymerizing a pre-gel reaction mixture comprising a humectant, an electrolyte, a first monomer, in which the first monomer is a mixture of acrylic acid and a salt thereof, and a second monomer, in which the second monomer is one of more monomers selected from $CH_2=CHC(O)XR$, in which X is O or NH and R is an unsubstituted or substituted alkyl group of 1 to 5 carbon atoms; polymerization initiator; neutralizer such as sodium hydroxide; water; and optionally, a crosslinking agent, and optionally, a polymerization inhibitor. The pH of the pre-gel reaction mixture, and of the resulting conductive composition, is typically about 7.0 or less, more typically about 3.0 to about 6.5, and even more typically about 3.0 to about 5.5. Medical electrodes comprising the conductive compositions meet ANSI/AAMI standard EC 12:2000, both before and after storage at 70° C. for 72 hours without packaging to prevent loss of water from the compositions. Medical electrodes comprising the conductive compositions of the invention have retained both their electrical and adhesive properties for up to five years on storage at ambient conditions without packaging to prevent loss of water from the composition.

The pre-gel reaction mixture comprises a humectant or a mixture of humectants. The humectant is preferably a non-volatile, non-toxic, water soluble or water miscible viscous liquid at room temperature. Typical humectants include polyhydric alcohols such as glycerin, sorbitol, ethylene glycol, propylene glycol, polyethylene glycols such as PEG 400 and PEG 600, poly(propylene glycol), and mixtures thereof. Preferred humectants include polyethylene glycol, sorbitol, and glycerin. The mixture typically comprises about 33 wt % to 68 wt %, typically 35 wt % to 65 wt %, more typically 55 wt % to 65 wt %, of the humectant.

The pre-gel reaction mixture comprises an electrolyte or a mixture of electrolytes. The electrolyte is typically a salt, such as lithium chloride, sodium chloride, potassium chloride, magnesium acetate, ammonium acetate, or a mixture thereof. A preferred electrolyte is potassium chloride. The mixture comprises about 0.5 wt % to about 10 wt %, typically about 1 wt % to about 8 wt %, more typically about 2.0 wt % to about 6 wt % of the electrolyte.

The pre-gel reaction mixture comprises a monomer mix. The monomer mix comprises a first monomer, a second monomer, and, optionally, a cross-linking agent. The first monomer is acrylic acid, a salt thereof, or a mixture thereof. The polymer produced by polymerization comprises acid acrylate moieties ($-CO_2H$ and/or $-CO_2M$, in which M is a cation such as sodium ion, potassium ion, lithium ion, ammonium or substituted ammonium ion, etc.) directly attached to the polymer backbone.

The second monomer is one of more monomers selected from $CH_2=CHC(O)XR$, in which X is O or NH and R is an unsubstituted or substituted alkyl group of 1 to 5 carbon atoms. The polymer produced by polymerization comprises groups of the structure $-C(O)XR$ directly attached to the polymer backbone.

Typical unsubstituted alkyl groups are methyl, ethyl, n-propyl, n-butyl, and n-pentyl. Typical substituents that may be present in a substituted alkyl group are halo (such as F, Cl, or Br) cyano, carboxylic acid and salts thereof (i.e., $-CO_2H$ or $-CO_2M$, in which M is a cation), phosphate and salts thereof, and sulfonic acid and salts thereof. An example of such a substituted alkyl group is (3-sulfopropyl)acrylic acid ester, potassium salt. A preferred second monomer is 2-acrylamido-2-methylpropane sulfonic acid ($CH_2=CH-CONHC(CH_3)_2-CH_2-SO_3H$) and/or a salt thereof. Typical salts are the sodium, lithium, potassium, ammonium, and substituted ammonium salts, and mixtures thereof.

The monomer mix typically comprises about 18 wt % to about 45 wt %, typically about 20 wt % to 40 wt %, of the of the pre-gel reaction mixture. Following the polymerization reaction, the resulting conductive composition comprises about 18 wt % to about 45 wt %, typically about 20 wt % to 40 wt %, of the copolymer. In the calculation of the percentage composition, acrylic acid and acrylic acid salt or salts are calculated as acrylic acid, and when 2-acrylamido-2-methylpropane sulfonic acid and/or a salt or salts thereof are present, they are calculated as the sodium salt of 2-acrylamido-2-methylpropane sulfonic acid (NaAMPS).

The first monomer makes up about 80 mol % to about 95 mol %, typically about 85 mol % to about 95 mol %, of the monomers present in the monomer mix (i.e., the total amount of the first monomer and the second monomer present in the monomer mix). The second monomer makes up about 5 mol % to about 20 mol %, typically about 5 mol % to about 15 mol %, of the monomer mix. In one embodiment the acrylic acid and/or salt or salts thereof make up about 90 mol % and the second monomer, such as 2-acrylamido-2-methylpropane sulfonic acid and/or salt or salts thereof, make up about 10 mol % of the monomer mix.

In one embodiment, the second monomer is 2-acrylamido-2-methylpropane sulfonic acid sodium salt (NaAMPS) ($CH_2=CH-CONHC(CH_3)_2-CH_2-SO_3^-M^+$). The first monomer (acrylic acid and/or salt or salt thereof, calculated as acrylic acid) comprises about 60 wt % to about 85 wt %, typically about 70 wt % to about 80 wt %, of the total amount of first monomer and the NaAMPS in the monomer mix. The NaAMPS (calculated as NaAMPS) comprises about 15 wt % to about 40 wt %, typically about 20 wt % to about 30 wt % of the total amount of first monomer and NaAMPS in the monomer mix. In one embodiment, the first monomer comprises about 70 wt % to 75 wt % and the NaAMPS comprises about 25 wt % to 30 wt % of the total amount of first monomer and NaAMPS in the monomer mix.

Optionally, the pre-gel reaction mixture may comprise an effective amount, typically 1 wt % or less, of a cross-linking agent or mixture of cross-linking agents. An effective amount of cross-linking agent is an amount that produces a conductive composition with the desired physical properties, such as coherence and adhesion, and electrical properties. Although the amount required will depend on, for example, the molecular weight of the cross-linking agent, the number of ethylenically unsaturated, free radical polymerizable groups present in the cross-linking agent, the amount of free radical polymerizable monomers present in the monomer mix, when the cross-linking agent is present, the amount of crosslinking agent will equal about 0.01 wt % to 1 wt %, more typically 0.02 wt % to 0.08 wt %, of the total weight of the first and second monomers, calculated as described above. The crosslinking agents are free radical polymerizable monomers that comprise more than one ethylenically unsaturated, free radical polymerizable group. Preferably the effective amount of crosslinking agent is soluble in the mixture. Numerous crosslinking agents polymerizable by free-radical initiated polymerization are known to those skilled in the art, Crosslinking agents include, for example, bis-acrylamides and methacrylamides, such as N,N'-methylene bis-acrylamide; acrylate and methacrylate esters of polyols, such as, ethylene glycol diacrylate and dimethacrylate, diethylene glycol diacrylate and dimethacrylate, trimethylolpropane triacrylate and trimethacrylate, ethoxylated trimethylolpropane triacrylate and trimethacrylate; pentaerythritol triacrylate and trimethacrylate, pentaerythritol tetraacrylate and tetramethacrylate, and polyethylene glycol diacrylates and dimethacrylates, such as the diacrylates and dimethacrylates of polyethylene glycols having a molecular weight of from about 200 to about 600. An especially useful crosslinking agent is N,N'-methylene bis-acrylamide [$(CH_2=CHCONH)_2CH_2$].

The crosslinking-agent may be added to the pre-gel reaction mixture, as, for example, a 1% solution in water. The amount of crosslinking agent is calculated as the amount of the crosslinking agent added, not as the amount of solution containing crosslinking agent added. The water in which the crosslinking agent is dissolved is counted as part of the water present in the mixture.

Although a crosslinking agent may be used to prepare the copolymer, it has been discovered that a conductive composition with the desired physical and electrical properties can be prepared without the use of a cross-linking agent. That is, the resulting copolymer is not crosslinked by a cross-linking monomer (i.e., a copolymer not crosslinked by a crosslinking agent).

The pre-gel reaction mixture comprises an effective amount of a polymerization initiator. An effective amount is an amount that produces efficient polymerization of the monomers under the polymerization conditions to produce a conductive composition with the desired physical and chemical properties. Numerous free radical polymerization initiators are known to those skilled in the art. The polymerization initiator may be a single compound or a mixture of compounds. Thermal and/or photo free radical polymerization initiators, for example, may be used. Typical thermal free radical polymerization initiators include azo compounds, such as 2,2-azobisisobutyronitrile (AIBN). Suitable photo free radical polymerization initiators are disclosed in "Photoinitiators for Free-Radical-Initiated Photoimaging Systems," by B. M. Monroe and G. C. Weed, *Chem. Rev.*, 93, 435-448 (1993) and in "Free Radical Polymerization" by K. K. Dietliker, in *Chemistry and Technology of UV and EB Formulation for Coatings, Inks, and Paints*, P. K. T. Oldring, ed, SITA Technology Ltd., London, 1991, Vol. 3, pp. 59-525. Typical free radical photo polymerization initiators include, for example, 1-hydroxycyclohexylphenyl ketone (HCPK, IRGACURE® 184); 2-hydroxy-2-methyl-1-phenylpropan-1-one (DAROCUR® 1173); 2-hydroxy-1-[4-(2-hydroxyethoxy)phenyl]-2-methyl-1-propan-1-one (IRGACURE®2959), 2,2-dimethoxy-2-phenylacetophenone (benzildimethyl ketal, BDK, IRGACURE®651), and a mixture of 50 wt % benzophenone and 50 wt % of 1-hydroxycyclohexylphenyl ketone (IRGACURE® 500). The pre-gel reaction mixture typically comprises less than about 1.0 wt %, more typically less than about 0.7 wt %, and even more typically less than about 0.4 wt %, of the polymerization initiator.

The pre-gel reaction mixture may comprise a neutralizer. Bases such as hydroxides, amines, Lewis bases, and mixtures thereof may be uses as neutralizers. The neutralizer is typically a base such as ammonium hydroxide, sodium hydroxide, potassium hydroxide, and/or lithium hydroxide. If the acrylic acid and/or the second monomer, such as the 2-acrylamido-2-methylpropane sulfonic acid, are added to the mixture at least partly in the acid form, it may be necessary to added neutralizer to the mixture to neutralize some of the acid so that the pH of the mixture is preferably about 3.0 to about 6.5. In one embodiment, all the 2-acrylamido-2-methylpropane sulfonic acid in the pre-gel reaction mixture is neutralized (i.e., present as a salt rather than as the acid), so 2-acrylamido-2-methylpropane sulfonic acid may be added to the pre-gel reaction mixture and neutralized by addition of a neutralizer. Alternatively, a salt or salts of the second monomer, such as the sodium salt, may be added so that the addition of a neutralizer to convert the acid form of the second monomer to a salt is unnecessary. Typically, only part of the acrylic acid is neutralized (i.e., present as a salt). Consequently, if acrylic acid is added, a neutralizer may be necessary to convert part of the acrylic acid to a salt or a mixture of salts. Alternatively, an appropriate mixture of acrylic acid and a salt or a mixture of salts may be added so addition of a neutralizer to convert part of the acrylic acid to a salt or mixture of salts is unnecessary. Typically about 10 mol % to about 60 mol % of the acrylic acid, more typically about 25 mol % to about 50 mol % of the acrylic acid is present in the pre-gel reaction mixture as a salt.

When acrylic acid and NaAMPS are present in the pre-gel reaction mixture, a neutralizer, typically sodium hydroxide, is added. The amount of neutralizer added is less than the amount necessary to neutralize all the acrylic acid in the mixture, so that the resulting mixture has a pH of about 3.0 to about 6.5. Typically about 10 mol % to about 60 mol % of the acrylic acid, more typically about 25 mol % to about 50 mol % of the acrylic acid is neutralized by the neutralizer.

When sodium hydroxide is used as the neutralizer, about 2 wt % to 8 wt % sodium hydroxide (dry weight) is added to the mixture. The sodium hydroxide may be conveniently added to the mixture as a water solution, such as, for example, an aqueous 50 wt % sodium hydroxide solution.

Water is present in the mixture. The amount of water includes any water present in any of the ingredients and any water added with ingredients that are in water solution, such as the monomers, the crosslinking agent, the neutralizer, the humectant, etc.

As will be apparent to those skilled in the art, when neutralizer is added to neutralize acrylic acid and/or the second monomer, water will be generated by the neutralization reaction. When the water produced by the neutralization reaction, if any, is included, the mixture comprises about 6 wt % to about 20 wt % water. When the water produced by partial neutralization of the acrylic acid is not included, the mixture comprises about 5 wt % to about 18 wt % water.

In addition to the free radical initiator, small amounts of free radical polymerization inhibitors may be present in one or more of the monomers, and/or the crosslinking agent, and/or may be added to the mixture to prevent premature polymerization of the reaction mixture. Typical free radical polymerization inhibitors include, for example, hydroquinone, 4-methoxyphenol, di-t-butyl-p-cresol, pyrogallol, t-butyl catechol, benzoquinone, 4,4'-thio-bis-(3-methyl-6-t-butylphenol), and 2,2'-methylene-bis-(4-methyl-6-t-butylphenol). When present, the amount of the polymerization inhibitor used is preferably about 0.01 wt % to about 5 wt % of the mixture. Other conventional ingredients of conductive compositions may be present in the pre-gel reaction mixture or added to the conductive composition following the polymerization reaction.

The pre-gel reaction mixture may be spread or coated as a layer on a release liner, for example a siliconized release substrate such as silicone coated polyethylene terephthalate film, or other substrate prior to polymerization. Free radical polymerization may be initiated by, for example, heating the mixture when a thermal free radical polymerization initiator is present in the mixture, or exposing the mixture to actinic radiation when a photoinitiated free radical polymerization initiator is present in the mixture. Any convenient source or sources of actinic radiation providing wavelengths in the region of the spectrum that overlap the absorption bands of the photoinitiated free radical polymerization initiator can be used to activate polymerization. The radiation can be natural or artificial, monochromatic or polychromatic, incoherent or coherent, and for high efficiency should correspond closely in wavelengths to the absorption bands of the polymerization initiator. Conventional light sources include fluorescent lamps, mercury vapor lamps, metal additive lamps, and arc lamps. Useful lasers are those whose emissions fall within or overlap the absorption bands of the photoinitiated free radical polymerization initiator. Although, if desired, the mixture may be degassed before polymerization and/or the polymerization may be carried out under an inert atmosphere, it is not necessary to degas the mixture before polymerization or to carry out the polymerization under an inert atmosphere.

Following polymerization, the resulting conductive composition may transferred to a conductive substrate. Alternatively, the conductive composition may be adhered to a conductive substrate, and the release liner left in place to protect the conductive composition until it is ready for use.

Medical Electrodes

Medical electrodes transmit electrical signals or currents to or from a patient's skin and an external medical apparatus. Medical electrodes are well known to those skilled in the art. Their construction is described, for example, in Dietz, U.S. Pat. No. 5,779,632, the disclosure of which is incorporated herein by reference. These electrodes typically comprise a conductive composition on a substrate. The layer of conductive composition can be adhered to or contacted with the skin of the patient. The medical electrode also comprises a conductive interface that is electrically connected to the layer of conductive composition and adapted to be electrically connected to an item of external medical equipment. For many applications, the conductive composition must also be sufficiently adhesive to adhere to the patient's skin, i.e., be a conductive adhesive. The configuration of the electrode and the adhesive properties required will depend on the intended application, such as whether the electrode is a transmission electrode, i.e., an electrode that sends electric currents or signals to the patient's body, or a sensing or monitoring electrode, i.e., an electrode that sends electrical signals from the patient's body to the external medical equipment.

Figure 2:
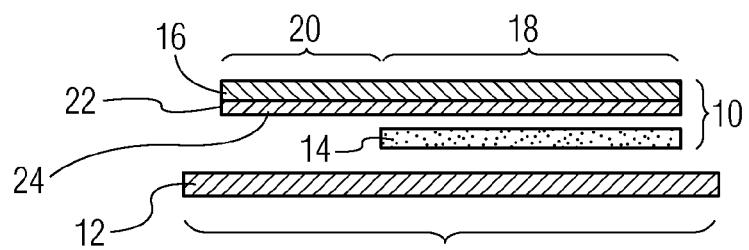
FIG. 2 is a cross-sectional view of the medical electrode of FIG. 1.

FIG. 1 and FIG. 2 show a medical electrode 10 on release liner 12. Release liner 12 is a release paper or film of a waxed or coated plastic, such as a silicone coated polyethylene terephthalate film, which is typically used to protect medical electrode 10 before application of the electrode to a skin surface.

Electrode 10 comprises layer of conductive composition 14. Electrode 10 also comprises conductive interface 16 comprising a conductor member having a conductive portion 18 contacting layer of conductive composition 14 and tab portion 20 extending beyond layer of conductive composition 14 for mechanical and electrical contact with the external medical equipment, such as a electrocardiogram monitoring (ECG) machine, an electroencephalogram (EEG) machine, or a transcutaneous electrical nerve stimulation (TENS) machine (not shown). Conductive interface 16 comprises conductive layer 24, coated on at least side 22 of conductive interface 16. Conductive layer 26 contacts layer of conductive composition 14. Medical electrode 10 can be used either as a diagnostic electrocardiogram (ECG or EKG) electrode or as a transcutaneous electrical nerve stimulation (TENS). In use, release liner 12, if present, is removed. Then layer of conductive composition 14 of electrode 10 is applied to the surface of the patient's skin and electrically connected to the external medical equipment.

Figure 3:
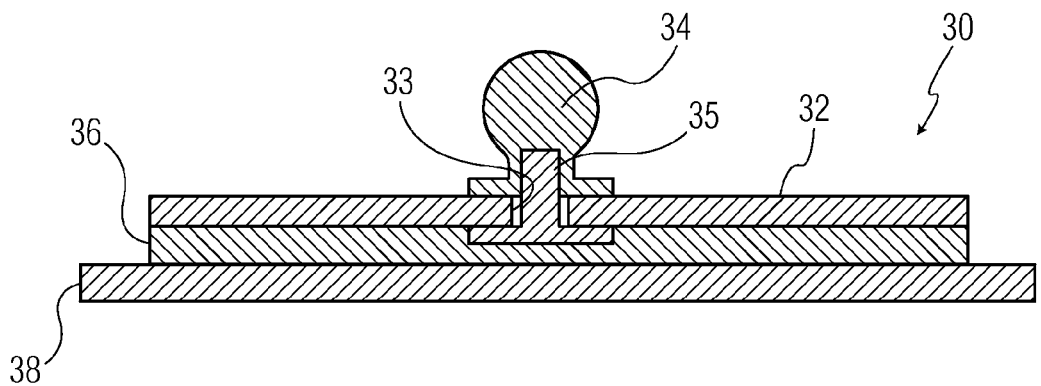
FIG. 3 is a cross-sectional view of a snap medical electrode.

FIG. 3 shows a cross-section of snap medical electrode 30 on a release liner. Electrode 30 has nonconductive backing 32, which has opening 33 covered by snap 34 through which eyelet 35 protrudes. Snap 34 is secured to eyelet 35. Together snap 34 and eyelet 35 comprise at least part of a conducive interface adapted to provide an electrical connection between layer of conductive composition 36 and the external medical equipment (not shown). Eyelet 34 and backing 32 are covered by layer of conductive composition 36. Release liner 38 protects the layer 36 of conductive composition prior to use.

The conductive compositions of the invention and medical electrodes comprising the compositions meet ANSI/AAMI standard EC 12:2000 for medical electrodes both before and after storage at 70° C. for 72 hours without packaging to prevent loss of water from the composition, which is equivalent to storage at 20° C. for about 96 days without packaging to prevent loss of water. Medical electrical comprising the conductive compositions of the invention have retained both their electrical and adhesive properties for up to five years on storage at ambient conditions without packaging to prevent loss of water from the composition.

The medical electrode may be packaged for use in a sealed or unsealed envelope of any of a number of suitable materials such as polyethylene or other plastic film. Because the properties of the conductive compositions of this invention do not change significantly when the electrode is stored open to the atmosphere, packaging is only necessary for product identification and to prevent contamination; foil barrier packaging is not required.

INDUSTRIAL APPLICABILITY

The conductive compositions of the invention are especially useful in medical electrodes that can be used with medical equipment for a variety applications, such as: electrocardiogram monitoring (ECG) electrodes (tab and snap style) for monitoring heart activity and for diagnosing heart abnormalities; electroencephalogram (EEG) electrodes; transcutaneous electrical nerve stimulation (TENS) electrodes used for pain management; neuromuscular stimulation (NMS) used for treating conditions such as scoliosis; muscle stimulation electrodes; wound treatment electrodes (accelerated healing of skin wounds or broken bones); defibrillation electrodes to dispense electrical energy to a chest cavity of a mammalian patient to defibrillate heart beats of the patient; and dispersive electrodes to receive electrical energy dispensed into an incision made during electrosurgery. Other applications of the conductive compositions of the invention include, for example, electro-surgical dispersive pads; drug delivery (passive or iontophoretic); pre-surgical limb or area markers, tapes (anchoring chest tubes, NG tubes, IVs, cannulae, etc); and sterile seals at needle or cannula entry points. The medical equipment used in these applications is well known to those skilled in the art.

The advantageous properties of this invention can be observed by reference to the following examples, which illustrate but do not limit the invention.

EXAMPLES

| Glossary | |
|---|---|
| AMPS | 2-Acrylamido-2-methylpropane sulfonic acid ($CH_2$=CHCONH—C($CH_3$)$_2$—$CH_2$—$SO_3$H) |
| D1173 | DAROCURE ® 1173 (2-Hydroxy-2-methyl-1-phenyl-propan-1-one) (Ciba Specialty Chemicals) |
| I-184 Solution | 3 wt % IRGACURE ® 184 (1-hydroxycyclohexylphenyl ketone) in 2-propanol (Ciba Specialty Chemicals) |
| Glycerin/NaCl Solution | 93.3% glycerin, 6.54% sodium chloride, and 0.08% deionized water |
| MBA Solution | 1 wt % N,N'-Methylene bis-acrylamide in water |

-continued

| | Glossary |
|---|---|
| Monomer Mix A | Mixture of 72.8% acrylic acid, 25.2% sodium salt of 2-acrylamido-2-methylpropane sulfonic acid (NaAMPS) and 2.0% water |
| 4-MPH | 4-Methoxyphenol |
| Neutralizer | 50 wt % Sodium hydroxide in water |

Examples 1-12

Preparation of the conductive compositions. The components listed in Table 1 were mixed together to form pre-gel reaction mixtures. The ingredients were added in the following order: monomer mix A, MBA solution, electrolyte (lithium chloride, sodium chloride, or potassium chloride), neutralizer, humectant (glycerol), and photoinitiator (I-184 solution). The mix time depended on the volume. When all components were completely dissolved and/or the mixture was homogenous, the pre-gel reaction mixture was coated onto a substrate with or without a scrim. The layer of the mixture has a thickness of about 0.01 to 0.25 inches. The pre-gel reaction mixture can also be injected into a retaining ring or mold directly and polymerized.

TABLE 1[a]

| Example | Monomer Mix A | MBA Soln[b] | LiCl | NaCl | KCl | Glycerol | 50% NaOH | % Acrylic Acid Neutralized |
|---|---|---|---|---|---|---|---|---|
| 1 | 50.0 | 3.0 | 1.3 | — | — | 40.00 | 5.20 | 13% |
| 2 | 15.0 | 3.0 | 2.0 | — | — | 74.90 | 4.60 | 38% |
| 3 | 20.0 | 3.0 | 2.0 | — | — | 69.44 | 5.06 | 31% |
| 4 | 20.0 | 4.0 | 2.0 | — | — | 68.50 | 5.00 | 31% |
| 5 | 20.0 | 4.0 | — | — | — | 70.00 | 5.50 | 34% |
| 6 | 20.0 | 5.0 | — | 1.0 | — | 68.00 | 5.50 | 34% |
| 7 | 20.0 | 7.0 | — | — | 1.0 | 65.50 | 6.00 | 37% |
| 8 | 20.0 | 7.0 | — | — | 2.0 | 64.50 | 6.00 | 37% |
| 9 | 20.0 | 6.5 | 1.0 | — | — | 66.00 | 6.00 | 37% |
| 10 | 20.0 | 8.0 | — | — | — | 65.61 | 5.88[a] | 37% |
| 11 | 20.0 | 7.0 | 2.0 | — | — | 64.49 | 6.00[a] | 37% |
| 12 | 40.0 | 6.0 | 2.0 | — | — | 40.49 | 11.00[a] | 34% |

[a]All compositions contained 0.5 wt % of I-184 solution. Examples 10, 11, and 12 also contained 0.01 wt % of 4-MPH.
[b]1 wt % N,N'-Methylene bis-acrylamide in water.

A pre-gel mixture that contained 20 wt % monomer mix, 3 wt % MBA, 1.5 wt % lithium chloride, 57.5 wt % of glycerol, 17.2 wt % of triethanolamine, 0.5 wt % of I-184, and 0.3 wt % of D1173 auto polymerized during preparation.

Preparation and Evaluation of Electrodes. Electrocardiogram snap electrodes were prepared from each composition. Each composition was coated onto a release substrate and polymerized using ultraviolet radiation from a xenon arc lamp. Then the resulting conductive composition was applied to a snap electrode substrate.

Accelerated aging was carried out by heating the electrodes at 70° C. in a forced draft oven with no packaging. Assuming that the rates of all the reactions that occur in the conductive composition are only dependent on temperature and applying the Arrhenius equation, 24 hours at 70° C. is equivalent to 32 days STORAGE at 20° C.

Performance standards have been drawn up by ANSI (American National Standards Institute) and AAMI (Association for the Advancement of Medical Instrumentation). The ANSI/AAMI standard, ANSI/AAMI standard EC 12:2000, incorporated herein by reference, is given in Table 2.

TABLE 2

| DC Offset (DCO) | Less than or equal to 100 mV |
|---|---|
| AC Impedance (ACZ) | Less than or equal to 2000 ohms |
| Slope | Absolute value is less than or equal to 1.0 mV/s |

Each electrode was tested on an Xtratek ET-65A ECG electrode tester (Xtratek, Lenexa, Kans., USA) or on an AngioLaz ECG electrode tester (AngioLaz, Bellows Falls, Vt.). The release liners were removed and pairs of electrodes were mated gel (layer of conductive composition) to gel (layer or conductive composition). All samples but Examples 5, 6, and 10 exceeded ANSI/AAMI standard EC 12:2000. Examples 5 and 10 have no electrolyte and Example 6 has only 1% electrolyte.

Samples 1-4 were placed in a 70° C. in a forced air oven for accelerated aging. After aging, each electrode tested met ANSI/AAMI standard EC 12:2000. This data is shown in Table 3.

TABLE 3

| | | | Defibrillation | | | |
|---|---|---|---|---|---|---|
| Example No. | DCO Mv | ACZ ohm | DCO mv | Slope mv/sec | ACZ ohm | |
| 1 | 2.6 | 633 | 22.7 | 0.5 | 659 | |
| 1 | 0.9 | 802 | 19.2 | 0.5 | 736 | After 2 weeks ambient |
| 1 | 0.4 | 882 | 17.5 | 0.5 | 830 | After 10 days at 70° C. |
| 2 | 0.5 | 450 | 15.6 | 0.4 | 420 | |
| 3 | 0.8 | 480 | 16.2 | 0.4 | 440 | |
| 4 | 2.2 | 560 | 16.4 | 0.5 | 480 | |
| 4 | 1.6 | 950 | 22.3 | 0.5 | 740 | After 36 days at 70° C. |
| 5 | 2.1 | 1294 | 372.2 | 3.2 | 1203 | |
| 6 | 6.9 | 961 | 65.9 | 3.1 | 843 | |
| 7 | 1.4 | 537 | 20.6 | 0.5 | 526 | |
| 8 | 0.2 | 448 | 16.2 | 0.4 | 429 | |
| 9 | 0.2 | 941 | 18.1 | 0.5 | 957 | |
| 10 | 6.6 | 1380 | 363.4 | 3.1 | 874 | |
| 11 | 0.2 | 198 | 16.3 | 0.3 | 476 | |
| 12 | 0.5 | 590 | 15.8 | 0.3 | 557 | |

The final set of data measures the adhesive quality of layer of the conductive composition. The tester is a Texture Technology's Texture Analyzer.

Texture Analyzer Data

| Example | Tack (g) | Area under curve (g-mm) | Leg length (mm) |
|---|---|---|---|
| 10 | 88.75 | 204.89 | 3.80 |
| 11 | 81.10 | 357.93 | 5.08 |
| 12 | 159.29 | 83.99 | 1.14 |

Examples 13-22

These Examples show the electrical and adhesive properties of conductive compositions of the invention. The conductive compositions were prepared as in Example 1, except that the sodium chloride was pre-dissolved in the glycerol. The Design of Experiments was a $2^5$, ¼ fractional factorial. There are eight examples (Examples 13-22) with two mid point repeats (Examples 21-22).

Measurements were made as in Example 1. The numbers reported are the average of twelve pairs of standard electrodes for each value. The first number reported is the initial DCO (DC offset) in millivolts. The next number reported is the ACZ (AC impedance) in ohms. Then each electrode goes through a series of four defibrillation pulses with the DCO and slope recorded after each pulse on each pair of electrodes. The next number reported is the maximum post defibrillation DCO, followed by the post defibrillation ACZ, and the maximum recovery slope in millivolt/second. These tests were performed on the gels one to two days after the films were made. These measurement were repeated on a second set of twelve pairs of standard ECG electrodes that had been heated for 72 hr at 70° C. in a forced draft oven with no packaging. This is equivalent to storage at 20° C. for about 96 days.

TABLE 4

| | Example No. | | | | |
|---|---|---|---|---|---|
| | 13 | 14 | 15 | 16 | 17 |
| Component | | | | | |
| Monomer Mix A | 20.000 | 20.000 | 20.000 | 20.000 | 40.000 |
| Glycerol | 67.222 | 63.190 | 59.704 | 63.231 | 37.191 |
| NaCl | 4.704 | 4.422 | 4.178 | 4.425 | 2.603 |
| MBA solution | 4.000 | 4.000 | 8.000 | 8.000 | 4.000 |
| DAROCUR ® 1173 | 0.030 | 0.300 | 0.030 | 0.300 | 0.030 |
| 50% NaOH soln. | 4.044 | 8.088 | 8.088 | 4.044 | 16.176 |
| Acrylic Acid Neutralized[a] | 25% | 50% | 50% | 25% | 50% |
| Electrical Responses | | | | | |
| Initial DCO (mV) | 0.532 | 0.409 | 0.567 | 0.397 | 1.015 |
| Initial ACZ (ohm) | 441.3 | 347.2 | 226.8 | 258.8 | 386.1 |
| Defib DCO (mV) | 14.5 | 14.9 | 13.6 | 13.9 | 14.3 |
| Defib ACZ (ohm) | 438.5 | 334.0 | 224.2 | 250.7 | 342.5 |
| Defib max slope (mV/sec.) | 0.15 | 0.15. | 0.15 | 0.15 | 0.16 |
| Aged for 72 hr at 70° C. Electrical Responses | | | | | |
| Initial DCO (mV) | 0.039 | 0.255 | 0.542 | 0.138 | 0.037 |
| Initial ACZ (ohm) | 110.5 | 80.1 | 90.5 | 42.5 | 97.9 |
| Defib DCO (mV) | 11.2 | 12.9 | 12.5 | 11.0 | 16.5 |
| Defib ACZ (ohm) | 98.7 | 38.1 | 78.2 | 63.9 | 91.0 |
| Defib max slope (mV/sec.) | 0.13 | 0.32 | 0.12 | 0.11 | 0.14 |
| Texture Analyzer | | | | | |
| Primary tack (grams) | 86.2 | 101.1 | 80.7 | 81.5 | 416.0 |

TABLE 4-continued

| | Example No. | | | | |
|---|---|---|---|---|---|
| | 18 | 19 | 20 | 21 | 22 |
| Component | | | | | |
| Monomer Mix A | 40.000 | 40.000 | 40.000 | 30.000 | 30.000 |
| Glycerol | 44.498 | 41.012 | 33.201 | 51.038 | 51.038 |
| NaCl | 3.114 | 2.870 | 2.323 | 3.571 | 3.571 |
| MBA solution | 4.000 | 8.000 | 8.000 | 6.000 | 6.000 |
| DAROCUR ® 1173 | 0.300 | 0.030 | 0.300 | 0.170 | 0.170 |
| 50% NaOH soln. | 8.088 | 8.088 | 16.176 | 9.221 | 9.221 |
| | 100.000 | 100.000 | 100.000 | 100.000 | 100.000 |
| Acrylic Acid Neutralized[a] | 25% | 25% | 50% | 38% | 38% |
| Electrical Responses | | | | | |
| Initial DCO (mV) | 0.607 | 0.427 | 0.386 | 0.948 | 1.005 |
| Initial ACZ (ohm) | 584.2 | 275.7 | 213.9 | 304.8 | 297.8 |
| Defib DCO (mV) | 12.8 | 11.7 | 14.5 | 13.0 | 13.2 |
| Defib ACZ (ohm) | 488.8 | 267.1 | 196.5 | 288.7 | 256.4 |
| Defib max slope (mV/sec.) | 0.14 | 0.13 | 0.15 | 0.14 | 0.14 |
| Aged for 72 hr at 70° C. Electrical Responses | | | | | |
| Initial DCO (mV) | 0.141 | 0.543 | 0.245 | 0.348 | 0.345 |
| Initial ACZ (ohm) | 106.9 | 140.3 | 164.0 | 152.3 | 157.3 |
| Defib DCO (mV) | 13.7 | 13.4 | 17.7 | 16.2 | 15.9 |
| Defib ACZ (ohm) | 96.7 | 109.7 | 135.4 | 139.0 | 142.0 |
| Defib max slope (mV/sec.) | 0.12 | 0.14 | 0.16 | 0.16 | 0.16 |
| Texture Analyzer | | | | | |
| Primary tack (grams) | 367.2 | 297.0 | 423.3 | 214.6 | 200.9 |

[a]Assumes complete reaction of the sodium hydroxide with the acrylic acid.

Additional sets of electrodes from Example 14 were heated at 70° C. in a forced draft oven with no packaging for a longer period of time to simulate storage at 20° C. for up to three years. The results of this accelerated aging are shown in Table 5.

TABLE 5

| | Calculated time at 20° C. (years) | | | | | |
|---|---|---|---|---|---|---|
| | 0[a] | 0.3[a] | 1.5 | 2.0 | 2.5 | 3.0 |
| Initial DCO (mV) | 0.4 | 0.3 | 0.3 | 0.4 | 0.4 | 0.2 |
| Initial ACZ (ohm) | 347 | 80 | 67 | 70 | 72 | 69 |
| Defib DCO (mV) | 14.9 | 12.9 | 13.7 | 13.2 | 13.3 | 14.2 |
| Defib ACZ (ohm) | 334 | 38 | 61 | 61 | 62 | 61 |
| Defib max slope (mV/sec.) | 0.15 | 0.3 | 0.4 | 0.4 | 0.4 | 0.4 |

[a]From Table 4.

Even after accelerated aging equivalent to three years storage without packaging at 20° C., the electrodes still met ANSI/AAMI standard EC 12:2000.

Comparative Examples 1-3

These Examples show the electrical properties of commercially available medical electrodes. The electrical properties of three commercially available medical electrodes were measured as described above. The electrical properties were measured before and after aging, open to the atmosphere, for 72 hours at 70° C. in a forced air oven. The water levels for each of the hydrogels are: 3M Red Dot™ Resting EKG Electrode, 38%; ConMed Model 1700 Medical Electrode, 38%; and Ambu Blue Sensor Medical Electrode, 84%.

The properties are give in Table 6 along with ANSI/AAMI standard EC 12:2000. Each value is the average of twelve determinations. After aging, open to the atmosphere, for 72 hours at 70° C., none of the three commercially available medical electrodes meets ANSI/AAMI standard EC 12:2000.

TABLE 6

|  | DC Offset Voltage (mv) | Impedance ACZ (ohms) | Defibrillation DCO (mv) | Overload ACZ (mv/sec) | Recovery Slope (mv/sec) |
|---|---|---|---|---|---|
| 3M Red Dot ™ Resting EKG Electrode |
| Initial | 0.2 | 287 | 12.8 | 265 | 0.12 |
| Aged[a] | 0.5 | 23,100 | 31.1 | 23,100 | 0.52 |
| ConMed Model 1700 Medical Electrode |
| Initial | 1.1 | 48 | 6.6 | 35 | 0.19 |
| Aged[a] | 0.6 | 23,100 | 27.8 | 23,100 | 0.34 |
| Ambu Blue Sensor Medical Electrode |
| Initial | 0.6 | 597 | 11.9 | 216 | 0.19 |
| Aged[a] | 0.6 | 23,100 | 0.6 | 23,100 | 0.01 |
| ANSI/AAMI Standard EC 12:2000 Limits |
|  | ≦100 | ≦2,000 | ≦100 | ≦2,000 | ≦1 |

[a]Aged for 72 hr at 70° C.

Example 23

This Example illustrates the preparation and the electrical properties of a conductive composition of the invention in which the co-polymer in the conductive composition is not cross-linked. A mixture of Monomer Solution A (40 g), glycerin/NaCl solution (35.52%), and deionized water (8.0 g) was cooled in an ice bath and mixed for about 10 minutes. Then 50% sodium hydroxide solution (16.18 g) was slowly added. The temperature must not exceed 45° C. during the addition. After all of the sodium hydroxide had been added, Darocur® D1173 (0.3 g) was added and the resulting mixture stirred for 10 minutes. The resulting pre-gel reaction mixture was converted to a gel as described in Example 1.

The electrical data properties for the conductive composition with no cross-linker are as follows:

N=6 (six pair of electrodes)
Initial DC Offset=0.35±0.20 millivolt (high=0.59; low=0.06)
Initial AC Impedance=532±18 ohm (high=565; low=515)
Defibrillation recovery DC Offset 16.4±2.0 (high=19; low=0.0)
Defibrillation Recovery Slope=0.42±0.01 mv/second (high=0.43; low=0.41)
Post Defibrillation AC Impedance=452±15 ohm (high=477; low=436)

Example 24

This Example illustrates the preparation and the electrical properties of a medical electrode containing a conductive composition of the invention before and after storage for over 5 years at room temp and humidity with no packaging.

A pre-gel reaction mixture was formed containing 50 wt % Monomer Solution A, 0.03 wt % of methylene-bis-acrylamide, 1.30 wt % of lithium chloride, 40.00 wt % of glycerol, 5.20 wt % 50% of sodium hydroxide solution, 0.50% of 3% Irgacure®184 in 2-propanol, and 2.97% deionized water. The resulting pre-gel reaction mixture contained 12.60 wt % of the sodium salt of 2-acrylamido-2-methylpropane sulfonic acid, 12.60 wt % of acrylic acid and its sodium salt; 0.03 wt % of MBA, 1.30 wt % of lithium chloride, 40.00 wt % of glycerol; 2.60 wt % of sodium hydroxide, 0.015 wt % Irgacure®184, 0.485 wt % of 2-propanol, and 6.57 wt % water, exclusive of water generated by neutralization of the acids with sodium hydroxide. The pre-gel reaction mixture was used to form a medical electrode, as described above.

The initial electrical properties of the medical electrode were (average of twelve pairs of electrodes): DCO=2.6 mV; ACZ=633 ohm; Defib. DCO=19.6 mV; Slope=0.5 mV/sec; and ACZ=730 ohm. After 5 years and 11 months at room temp and humidity with no packaging the electrical properties were (average of twelve pairs of electrodes): DCO=0.8 mV; ACZ=843 ohm; Defib. DCO=17.5 mV; Slope=0.5 mV/sec; and ACZ=763 ohm.

Having described the invention, we now claim the following and their equivalents.

What is claimed is:

1. A method for forming a conductive composition, the method comprising the steps of:
   a) preparing a pre-gel reaction mixture comprising:
      about 33 wt % to 68 wt % of a humectant;
      about 1 wt % to about 8 wt % of an electrolyte;
      about 2 wt % to 8 wt % sodium hydroxide;
      about 18 wt % to about 45 wt % of a monomer mix, the monomer mix comprising about 60 wt % to 85% of acrylic acid, about 15 wt % to 40 wt % of the sodium salt of 2-acrylamido-2-methylpropane sulfonic acid, in which part of the acrylic acid is neutralized by the sodium hydroxide to form sodium acrylate;
      a polymerization initiator;
      about 5 wt % to about 18 wt % water, exclusive of water formed by the neutralization of the part of the acrylic acid by the sodium hydroxide; and
   b) polymerizing the monomer mix to form a copolymer.

2. The method of claim 1 in which the pre-gel reaction mixture does not comprise a crosslinking agent.

3. The method of claim 2 in which the pre-gel reaction mixture comprises about 55 wt % to about 65 wt % of the humectant or the mixture of humectants and about 20 wt % to about 40 wt % of the monomer mix.

4. The method of claim 3 in which the monomer mix comprises about 70 wt % to about 80 wt % of the acrylic acid and sodium acrylate and about 20 wt % to about 30 wt % of the sodium salt of 2-acrylamido-2-methylpropane sulfonic acid.

5. The method of claim 4 in which the humectant is glycerol and the electrolyte is sodium chloride.

6. The method of claim 1 in which the pre-gel reaction mixture comprises a crosslinking agent.

7. The method of claim 6 in which the pre-gel reaction mixture comprises about 55 wt % to about 65 wt % of the humectant or the mixture of humectants and about 20 wt % to about 40 wt % of the monomer mix.

8. The method of claim 7 in which the monomer mix comprises about 70 wt % to about 80 wt % of the acrylic acid and sodium acrylate and about 20 wt % to about 30 wt % of the sodium salt of 2-acrylamido-2-methylpropane sulfonic acid.

9. The method of claim 8 in which the humectant is glycerol and the electrolyte is sodium chloride.

* * * * *